(12) United States Patent
Patterson et al.

(10) Patent No.: US 6,479,473 B1
(45) Date of Patent: Nov. 12, 2002

(54) LONG-ACTING ANTIMICROBIALS

(75) Inventors: Alan Patterson, Belfast (GB); Neil Orr, Down (GB)

(73) Assignee: Norbrook Laboratories Ltd. (GB)

( * ) Notice: Subject to any disclaimer, the term of this patent is extended or adjusted under 35 U.S.C. 154(b) by 0 days.

(21) Appl. No.: 09/381,069

(22) PCT Filed: May 6, 1997

(86) PCT No.: PCT/GB97/01222

§ 371 (c)(1),
(2), (4) Date: Feb. 23, 2000

(87) PCT Pub. No.: WO98/50045

PCT Pub. Date: Nov. 12, 1998

(51) Int. Cl.⁷ ................................................ A61K 31/65
(52) U.S. Cl. .................... 514/152; 514/352; 514/974; 424/405; 424/406
(58) Field of Search ................. 424/405, 422, 424/406; 514/974, 152, 352

(56) References Cited

FOREIGN PATENT DOCUMENTS

WO        WO 96/01634        1/1996

OTHER PUBLICATIONS

Lockwood, P.W. et al., "Flunixin–Meglumin als Zusatz zur antibiotischen Therapie: Die Wirksamkeit bei der Behandlung der enzootischen Pneumonie des Rindes unter den Bedingungen eines amerikanischen Feedlots," *Tierärztliche Umschau*, 52:127–131 (1997).

Dherty, M.L., et al., "Isolation of *Mycoplasma bovis* from a calf imported into the Republic of Ireland," *Veterinary Record*, 135:259–260 (1994).

Kopcha, M. et al., "Experimental uses of flunixin meglumine and phenylbutazone in food–producing animals," *J. Am.Vet. Med.. Assoc.*, 194:45–49 (1989).

Verhoeff, J. et al., "Flunixin meglumine in calves with natural bovine respiratory syncytial virus infection," *Veterinary Record*, 118:14–16 (1986).

*Primary Examiner*—Neil S. Levy
(74) *Attorney, Agent, or Firm*—Heslin Rothenberg Farley and Mesiti, P.C.; Candace J. Clement, Esq.

(57) ABSTRACT

A method for producing an improved veterinary product is disclosed. The method comprises bringing a selected long-acting anticmicrobial formulation into intimate admixture with a predetermined amount of an anti-inflammatory agent and preparing the admixture for parenteral administration.

4 Claims, No Drawings

LONG-ACTING ANTIMICROBIALS

CROSS REFERENCE TO RELATED APPLICATION

This application is a 35 USC §371 filing of PCT/GB97/01222, filed May 6, 1997, the entire contents of which is incorporated herein by reference.

FIELD OF THE INVENTION

This invention relates to administration of antimicrobials primarily in the field of veterinary medicine. The desirability of minimising administration activities in veterinary medicine is particularly acute for several reasons. Obviously the subject of treatment in veterinary medicine cannot be counselled nor cooperate in the treatment process. Therefore in addition to therapeutic considerations there arise disadvantages including the labour involved in catching and handling the animal and the stress it suffers arising from the treatment. One way of addressing these difficulties is to provide long-acting formulations so that each separate act of administration has a longer effect before a further treatment is called for.

BACKGROUND OF THE INVENTION

Long acting or single treatment antimicrobials have been available for some time now in veterinary medicine.

The long acting basis of such products can result from a combination of both the inherent nature of the drug or drug form used and the formulation in which it is administered. Their benefits over conventional repeat treatment products may include: reduced stress to the sick animal, in that it does not have to be caught and restrained on a daily basis in order to receive treatment, reduced work load for the farmer/veterinarian again because there are no repeat treatments and increased efficacy in treating clinical conditions in that drug levels are continuously present over a prolonged period.

However one of the problems with long acting formulations of antimicrobials is that they may cause irritation at the site of administration and also that high levels of antimicrobial can be found at the sites of administration for a long time.

A further difficulty with long acting or single treatment products can be that they may not give as high blood levels immediately following administration as do the repeat treatment products. Whilst this may not affect the overall level of efficacy of the product it may result in a slower initial rate of recovery which can in some cases lead to the increased rate of long term damage to affected tissues and organs. An alternative explanation for the cause of tissue/organ damage is that it results as a consequence of the animals own inflammatory response to infection. As well as causing damage to tissue this inflammatory process may also reduce the diffusion of antimicrobial to the site of infection/inflammation. One means of preventing this from happening is to administer an anti-inflammatory drug. Such a drug on its own will reduce the inflammatory response but will not reduce the incidence of bacterial infection and so it is also necessary to administer an antimicrobial. One such product containing both an anti-inflammatory drug and an antimicrobial is commercially available, namely, Finabiotic, Schering-Plough Animal Health, however, use of this product requires daily treatments in order to be effective.

SUMMARY OF THE INVENTION

Accordingly it is an object of the present invention to obviate or mitigate the aforesaid disadvantages by providing a long-acting or single treatment formulation which has both antimicrobial and anti-inflammatory effect.

According to this invention there is provided a veterinary product comprising an antimicrobial and an anti-inflammatory agent in intimate admixture wherein the antimicrobial is selected from the group consisting of long-acting antimicrobials or depot antimicrobial formulations.

The product is preferably provided as a single dosage in a pharmaceutically permissible "ready for use" container such as a multi use vial or as a disposable syringe, or in packaging (e.g. blister packaging) containing a selected number of discrete dosage formulations for a prescribed period of treatment, each formulation being contained in a multi use vial or in an ampoule or disposable dispensing device adapted for parenteral use or any other suitable physiologically acceptable carrier or vehicle.

Further according to the present invention there is provided a method of producing an improved veterinary product comprising bringing a selected amount of a long acting antimicrobial into intimate admixture with a pre-determined amount of an anti-inflammatory agent and preparing the admixture for parenteral administration. Preferably the amounts of antimicrobial and anti-inflammatory agent are calculated to provide dosage amounts for a single treatment.

Advantageously this invention provides a veterinary product which on administration produces reduced irritation at the site of administration and reduced levels of antimicrobial found at the sites of administration over a period of time.

DESCRIPTION OF THE PREFERRED EMBODIMENTS

The invention will now be further described by way of reference to the following examples:

EXAMPLE 1

Comparison of a Long-acting Antimicrobial Formulation with a Formulation Comprising a Long-acting Antimicrobial and an Anti-inflammatory Drug A trial was conducted to compare the efficacy of a long-acting antimicrobial formulation to a formulation comprising a long-acting antimicrobial and an anti-inflammatory drug. The active constituents of the two formulations are detailed in Table 1 below:

TABLE 1

Active constituents of formulations used in trial.

Active ingredients

| | |
|---|---|
| Control article | 300 mg/ml oxytetracycline in a long-acting formulation |
| Test article | 300 mg/ml oxytetracycline in a long-acting formulation containing 20 mg/ml flunixin |

The comparative efficacy of the formulations was tested using a controlled disease model of pneumonia in cattle. The object of the study was to evaluate whether the addition of anti-inflammatory drug imparted benefit to the test animals.

Sixteen cattle were inoculated over two consecutive days with cultures containing an isolate of Pasteurella haemolytica, serotype Al from a field case of bovine respiratory disease. This organism is one of the most common bacteria associated with respiratory disease in cattle. At 48 hours after initial inoculation, fourteen animals satisfied the requirements for selection for treatment (pyrexia >103.0° F. and obvious signs of respiratory disease). These animals were randomly allocated to two groups, seven animals per group. One group received a single administration of the test article (antimicrobial and anti-inflammatory), the other group receiving treatment with the control article (antimicrobial alone). Both products were administered at the same dose rate of 1 ml per 10 kg bodyweight on a single occasion. The study animals were maintained in their original pre-treatment pens and hence the animals from both groups were commingled in the same accommodation. The animals were closely monitored over the following days for response to treatment. This included detailed clinical examination at set timepoints by a veterinary surgeon blinded to the allocation to treatment groups. Body temperature, respiratory rate and the presence of clinical signs such as hyperpnoea (increased respiratory effort), dullness and respiratory sounds on auscultation using a stethoscope were recorded. An increase in body temperature and respiratory rate would indicate a developing respiratory disease, as would the recording of dullness, hyperpnoea and respiratory sounds. Using a pre-determined semi-quantitative weighted scoring system, the values for these five parameters were combined to give an overall score for each animal at each timepoint. The values were then summated to give a mean value per group per timepoint. The mean body temperature and total clinical score per group at timepoints considered to be representative of both short term and long term clinical efficacy are presented in Tables 2 and 3 below. The data was analysed using the Student t-test (paired and unpaired).

TABLE 2

Body temperature (° F.)

| Timepoint | Test Article (antimicrobials + anti-inflammatory) | Control Article (antimicrobials alone) |
|---|---|---|
| Pre-inoculation | 102.2 | 102.1 |
| Pre-treatment | 104.2 | 104.1 |
| Post treatment | | |
| 3 hours | 101.9 | 103.8 |
| 6 hours | 101.8 | 103.2 |
| 9 hours | 102.1 | 103.7 |
| 12 hours | 102.3 | 103.9 |
| 72 hours | 102.4 | 103.1 |
| 96 hours | 102.5 | 103.5 |
| 144 hours | 102.1 | 103.1 |

At the 3, 6, 9 and 96 hour post treatment timepoints, the values for the antimicrobial alone group were statistically significantly higher than the pre-inoculation value (paired t-test). At none of the above post treatment timepoints were the values for the combination product statistically significantly higher than the pre-inoculation values, indeed, at the 6 hour timepoint the values were significantly lower than the baseline values. Also, at the 3, 6, 9, 12 and 96 hour timepoints, the values for the test article group were statistically significantly lower than the values for the control article (unpaired t-test).

TABLE 3

Total Clinical Score

| Timepoint | Test Article (antimicrobial + anti-inflammatory) | Control Article (antimicrobial alone) |
|---|---|---|
| Pre-inoculation | 0.6 | 0.86 |
| Pre-treatment | 23.3 | 22.7 |
| Post treatment | | |
| 3 hours | 14.4 | 22.7 |
| 6 hours | 13.3 | 19.4 |
| 9 hours | 15.4 | 19.4 |
| 12 hours | 16.7 | 21.6 |
| 72 hours | 7.1 | 13.9 |
| 96 hours | 4.9 | 14.9 |
| 144 hours | 4.3 | 10.9 |

At only the last of the above post treatment timepoints (144 hours) were the values for the test group (antimicrobial alone) significantly lower than those immediately prior to the onset of treatment (paired t-test). However, at all of the above post treatment timepoints, with the exception of the 12 hour timepoint, the values for the combination product were statistically significantly lower than the values immediately prior to treatment. Also, at the 3, 6, 96 and 144 hour timepoints, the values for the test article group were statistically significantly lower than the values for the control article (unpaired t-test), the values at 72 hours being just outside statistically significance (P=0.06).

From this data, generated in a controlled acute disease model, it is clearly apparent that the combination of the long acting antimicrobial and anti-inflammatory drug had a significantly greater short term and long term therapeutic efficacy than the long acting antimicrobial alone.

EXAMPLE 2

Determination of the Levels of Antimicrobial in Tissue

A further trial was conducted using the formulations detailed in Table 1 to determine the levels of antimicrobial in tissue. One half of the animals received treatment with the control article at a dose rate of 1 ml per 10 kg bodyweight and the other half received the test article at the same dose rate i.e., 1 ml per 10 kg bodyweight. At 21 and 28 days following treatment, the muscle from the injection sites (of animals from both treatments) which received a dose volume in each case of 15 ml was removed for determination of the level of antimicrobial. The results are presented below as follows:

TABLE 4

| | Oxytetracycline concentration ($\mu g/g$) at site of administration | |
|---|---|---|
| | 21 days | 28 days |
| Control article | 4.33 | 0.67 |
| Test article | 0.038 | <0.025 |

As can be clearly seen from the results the levels of antimicrobials were considerably lower in the group treated with the test article.

EXAMPLE 3

Determination of the Degree of Irritation Following Injection

In a further study animals were again treated with the test and control articles of Table 1 at a dose rate of 1 ml per 10 kg bodyweight, in this case to determine the degree of irritation following injection. As well as receiving the control article, flunixin was administered as a separate formulation to the control group at a dose rate of 2 mg/kg bodyweight (the same dose as administered in the test article). Tissue irritation was assessed by means of the determination of the levels of the enzyme aspartate aminotransferase (AST). This enzyme is released when body tissues are damaged and so its level in plasma increases. The results of the trial are presented below as follows:

TABLE 5

| | AST Levels (u/l) After Administration: | | | | |
|---|---|---|---|---|---|
| | 0 hours | 6 hours | 24 hours | 48 hours | 96 hours |
| Control article flunixin at 2 mg/kg | 46 | 81 | 100 | 83 | 51 |
| Test article | 39 | 54 | 67 | 54 | 44 |

Clearly, it can be seen in Example 3 that the formulation of the present invention (the formulation containing the long acting antimicrobial in admixture with the anti-inflammatory drug) produced less irritation and/or tissue damage than did the long acting antimicrobial and anti-inflammatory when injected as separate products.

In the present invention the combination into one formulation of a long-acting or single treatment antimicrobial with an anti-inflammatory drug is completely novel and provides a single product which will be highly effective in the treatment of bacterial infections and associated anti-inflammatory reactions. The combination offers advantages by way of a more rapid and complete treatment of infection than delivery of either of the two individual components separately.

It should be noted that there are various possible combinations of a long-acting or single treatment antimicrobial with anti-inflammatory agent for use in veterinary medicine. In this invention the antimicrobial drug could usefully be a tetracycline, eg, oxytetracycline, a cephalosporin, or a penicillin, eg, ampicillin, amoxycillin, penicillin G or the like or a macrolide, eg, erythromycin, tylosin, tilmicosin or the like or an aminoglycoside, eg, dihydrostreptomycin or the like, or a sulphonamide or a diaminopyrimidine eg, trimethoprim, alone or in combination. Other antimicrobials may also be usefully employed where they can exist in long-acting or single treatment formulations. The anti-inflammatory drug could usefully be flunixin, nimesulide, phenylbutazone, ketoprofen, piroxicam, dexamethasone, flumethasone, betamethasone or other drug possessing anti-inflammatory capabilities.

It will be understood by those in this art that the invention is not restricted to the particular embodiment described above, and variants based on alternative antimicrobials/anti-inflammatory agents are within the scope of the invention which is to be defined by the claims appended hereto.

We claim:

1. A single treatment veterinary formulation comprising a therapeutically effective amount of a long-acting oxytetracycline formulation and an effective adjuvant amount of flunixin, in a pharmaceutically acceptable carrier for parenteral administration.

2. The single treatment veterinary formulation of claim 1, comprising 300 mg/ml oxytetracycline and 20 mg/ml flunixin.

3. A method of treating a microbial infection in an animal, the method comprising administering to an animal in need of antimicrobial treatment, a single parenteral dose of a single treatment veterinary formulation comprising a therapeutically effective amount of a long-acting oxytetracycline formulation and an effective adjuvant amount of flunixin, in a pharmaceutically acceptable carrier for parenteral administration.

4. The method according to claim 3, wherein the single treatment veterinary formulation comprises 300 mg/ml oxytetracycline and 20 mg/ml flunixin.

* * * * *